United States Patent [19]
Bennett

[11] Patent Number: 6,024,091
[45] Date of Patent: Feb. 15, 2000

[54] RESTRAINING GARMENT

[76] Inventor: James P. Bennett, 8823 Holly Dr., #M206, Everett, Wash. 98208

[21] Appl. No.: 09/107,337

[22] Filed: Jun. 30, 1998

[51] Int. Cl.[7] ....................................................... A61F 5/37
[52] U.S. Cl. ........................................... 128/873; 128/876
[58] Field of Search ..................... 128/845, 846, 128/869–876; 70/16

[56] References Cited

U.S. PATENT DOCUMENTS

| | | |
|---|---|---|
| D. 307,799 | 5/1990 | Worley ..................................... D24/34 |
| 1,047,457 | 12/1912 | Steimer . |
| 2,030,091 | 2/1936 | Behringer ................................ 128/873 |
| 2,425,489 | 8/1947 | Peterson . |
| 3,042,031 | 7/1962 | Reed ....................................... 128/876 |
| 3,502,073 | 3/1970 | Stanley . |
| 3,901,229 | 8/1975 | Hensel et al. . |
| 4,860,560 | 8/1989 | Lundelius . |
| 4,971,073 | 11/1990 | Schneider ............................... 128/874 |
| 5,016,650 | 5/1991 | Marlar . |

*Primary Examiner*—Michael A. Brown
*Attorney, Agent, or Firm*—Christensen O'Connor Johnson & Kindness PLLC

[57] ABSTRACT

The present invention provides a restraining garment for restraining a person. The restraining garment includes a body (10); a right sleeve (30) having a reinforced cuff (38) that is securable around the wrist of a wearer, a left sleeve (32) having a reinforced cuff that is securable around the wrist of a wearer; a right arm strap (46) extending from the body and securable to a portion of the right sleeve that is proximate to the cuff; and a left arm strap (48) extending from the body and securable to a portion of the left sleeve that is proximate to the cuff. The right and left arm straps, when secured to the cuffs of the right and left sleeves, respectively, restrain the movement of the arms of the wearer.

12 Claims, 3 Drawing Sheets

RESTRAINING GARMENT

FIELD OF THE INVENTION

This invention relates to restraining devices, in particular to rip-resistant, restraining garments that can be used to restrain a person.

BACKGROUND OF THE INVENTION

It is sometimes necessary to restrain certain persons, such as criminals and mentally disturbed persons, for their own protection and for the protection of others. One method of restraining a person is to use hand-cuffs which typically include a pair of metallic cuffs joined by a short chain. The cuffs can be locked around the wrists of a restrainee, thereby binding the restrainee's hands and wrists close together, either in front of, or behind, the restrainee's body. A variation on the traditional, metallic hand-cuffs are plastic flex-cuffs which include a flexible, plastic strip that is smooth on one side and serrated on the opposite side, and which defines a hole at one end. The flex cuff is applied to a restrainee by threading one end of the plastic strip through the hole at the other end of the plastic strip, thereby looping the flex cuff around the wrist or ankle of the restrainee. The flex cuff is drawn tight around the restrainee's wrist or ankle so that at least one of the serrations on one side of the plastic strip securely engage the portion of the plastic strip that defines the border of the hole. The flex cuff can only be removed by cutting the plastic strip.

A drawback associated with hand-cuffs and flex-cuffs is that, although the restrainee's hands are securely bound together, the restrainee is still capable of relatively unhindered arm movement and, especially if the hands are bound in front of the restrainee's body, can use his or her arms and bound hands as weapons. One solution to the problem of restraining both the hand and arm movement of a restrained individual is to apply securable cuffs, such as hand-cuffs or cuffs having a hook-and-loop fastener, such as Velcro, to the wrists of the restrainee and attaching the cuffs to a belt worn around the restrainee's waist. A problem with this type of device, however, is that the restrainee, especially a thin restrainee, can slide out of the belt.

Another solution to the problem of restraining both the hand and arm movement of a restrained individual is a strait-jacket which is a garment, typically manufactured from canvas, having arms that are sealed at the wrists so that the wearer's hands are trapped within the sleeves. The sleeves are secured to the rear portion of the strait jacket so that the wearer's arms are wrapped around his or her torso. The strait-jacket thus completely immobilizes the hands and arms of the wearer.

Restraining devices such as hand-cuffs, flex-cuffs and strait-jackets may, however, be inhumane when continuously applied for an extended period. For example, a prisoner being transferred from one penal institution to another is typically restrained during the entire transfer period in order to prevent escape. Further, restraining devices, such as hand-cuffs, flex-cuffs and strait-jackets, provide the person in charge of the restrainee with only a limited ability to vary the degree of restraint applied to the restrainee.

Restraining devices can also serve a rehabilitative function. Thus, for example, a troublesome prison inmate can be completely restrained by means of, for example, a strait-jacket, during periods of misbehavior, but can be provided with an incentive to conform to the rules by the prospect of a less onerous form of restraint. Further, prison inmates who are being moved by public transport often do not want to be seen to be restrained. They have an incentive to behave if their good behavior is rewarded by the use of a restraining device which is not readily visible to a casual observer.

Thus, there is a need for a restraining garment that provides the person in charge of the restrainee with the ability to vary the degree of restraint applied to the restrainee, and which permits the restrainee a reasonable degree of limb movement during extended periods of restraint. Further, the garment should present the appearance of a normal, everyday item of clothing that does not attract the attention of a casual observer to the fact that the wearer is under restraint.

SUMMARY OF THE INVENTION

The present invention provides a restraining garment for restraining a person. The restraining garment includes a body; a first sleeve having a proximal end, attached to the body, and a distal end; a second sleeve having a proximal end, attached to the body, and a distal end; a first arm strap capable of connecting the body to a portion of the first sleeve that is closer to the distal end of the first sleeve than to the proximal end of the first sleeve, and a second arm strap capable of connecting the body to a portion of the second sleeve that is closer to the distal end of the second sleeve than to the proximal end of the second sleeve. The first and second arm straps, when secured to the first and second sleeves, respectively, restrain the movement of the arms of the wearer. The body further includes at least one attachment site for securing one or both arms of the wearer close to the body by means of a securing device, such as a padlock. Each of the first and second arm straps has a length that is insufficient to permit a garment wearer to fully extend the first or second sleeve to form a right angle with respect to the body when the first and second arm straps are connected to the first and second sleeves, respectively.

A preferred embodiment of the present invention provides a restraining garment, made from rip-resistant material, in the form of a shirt having a body, a first sleeve and a second sleeve. The body includes a front portion, a rear portion, a first side portion and a second side portion. The first and second sleeves each include a proximal end attached to the shoulder region of the body, and a distal end including a reinforced cuff. The body further includes a plurality of rigid loops securely attached to the front portion of the body along its vertical midline. Additional rigid loops are securely attached to the rear portion of the body at each of the shoulders and on the vertical midline. Reinforced holes penetrate the left and right halves of the collar, and each of the sleeves immediately adjacent the reinforced cuffs. The rigid loops and reinforced holes serve as attachment sites for a securing device, such as a padlock A first arm strap includes a proximal end and a distal end. The first arm strap proximal end is attached to the first side portion of the body, and each of the proximal end and the distal end of the first arm strap define a plurality of slots. Additionally, the terminal portion of the distal end of the first arm strap further includes a rigid loop. A second arm strap, identical in structure and operation to the first arm strap, is attached at its proximal end to the second side portion of the body. Additionally, two crotch straps, each having a first end and a second end, are attached by the first end to an area of the front portion of the body close to its lower margin. Both of the crotch straps include a plurality of slots proximate to their second ends. The slots defined by the first and second arm straps, and by the crotch straps, serve as attachment sites for a securing device, such as a padlock.

In operation, the shirt is pulled over the head of the wearer, with the arms being inserted into the sleeves. Thus, the front portion of the shirt is adjacent the front of the wearer's torso, the rear portion of the shirt is adjacent the back of the wearer's torso, the first sleeve covers the wearer's right arm and the second sleeve covers the wearer's left arm. The wearer's right hand protrudes through the cuff of the first sleeve, the wearer's left hand protrudes through the cuff of the second sleeve, and the wearer's head protrudes through the collar which is disposed around the wearer's neck. The designations "right" and "left" are as conventionally defined from the perspective of a wearer of the restraining shirt.

To tether the wearer's right arm to the body of the shirt, the distal end of the first arm strap is inserted into one end of the passage defined by the reinforced cuff of the first sleeve until the rigid loop attached to the terminus of the first arm strap distal end protrudes out of the other end of the cuff passage. A securing device, preferably a padlock, is inserted through the loop attached to the terminus of the first arm strap distal end, and also through one of the slots defined by the distal portion of the first arm strap. The slot through which the padlock is inserted is selected so that the cuff is drawn around the wrist of the wearer sufficiently tightly to prevent the wearer from withdrawing his or her hand through the sleeve, but not so tightly that the circulation of the blood through the hand is impeded. If it is necessary to further secure the wearer's arm within the sleeve, a securing means, preferably a padlock, can be inserted through the reinforced holes penetrating the sleeve close to the reinforced cuff. A similar procedure is followed to secure the wearer's left arm within the second sleeve of the restraining shirt.

The extent of the wearer's arm movement can be adjusted by shortening the length of either or both of the first and second arm straps. This is achieved by inserting a securing device, preferably a padlock, through at least two of the slots defined by the portion of each of the arm straps adjacent the body. Thus, for example, by inserting a padlock through the first and last of the slots defined by the proximal end of the first arm strap, the wearer's right arm is restrained close to the body and the degree of arm movement is minimized. The wearer's arm movements can be further restricted by using a securing device, such as a padlock, to attach either or both of the sleeves to a rigid loop located on the front or rear portions of the body of the shirt.

The wearer is prevented from pulling the shirt over his or her head by the two crotch straps that are attached, at their first ends, close to the lower margin of the front portion of the shirt. The two crotch straps extend between the legs of the wearer and are secured, preferably by a padlock inserted through one of the slots defined by the second end of each of the crotch straps, to rigid loops located on the shoulder regions of the rear portion of the shirt body. The wearer may optionally be further secured within the shirt by inserting a securing device, preferably a padlock, through each of two, reinforced holes defined by the front portion of the collar of the shirt.

The present invention thus provides a rip-resistant, restraining garment that provides the person in charge of the wearer of the shirt with the option of applying several degrees of restraint to the movement of the wearer's arms. The restraining garment of the present invention may therefore be used to severely restrict the movement of the wearer's arms when the wearer behaves in a violent or inappropriate manner. Conversely, the restraining garment of the present invention may be used to minimally restrain the movement of the wearer's arms when the wearer behaves appropriately. Thus the restraining garment of the present invention provides the wearer with an incentive to behave in an acceptable manner since such behavior will result in a minimal degree of restraint. Further, the restraining garment of the present invention is tailored to have the appearance of a normal article of clothing so that it is not apparent to a casual observer that the wearer is under restraint.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As used herein, the designations "right" and "left" are as conventionally defined from the perspective of a wearer of the restraining garment of the present invention.

The present invention provides a restraining garment for restraining a person. The restraining garment includes a body; a first sleeve having a proximal end attached to the body, and a distal end; a second sleeve having a proximal end attached to the body, and a distal end; a first arm strap extending from the body and securable to a portion of the first sleeve that is closer to the distal end of the first sleeve than to the proximal end of the first sleeve, and a second arm strap extending from the body and securable to a portion of the second sleeve that is closer to the distal end of the second sleeve than to the proximal end of the second sleeve. The first and second arm straps, when secured to the first and second sleeves, respectively, restrain the movement of the arms of the wearer.

Figure 1:
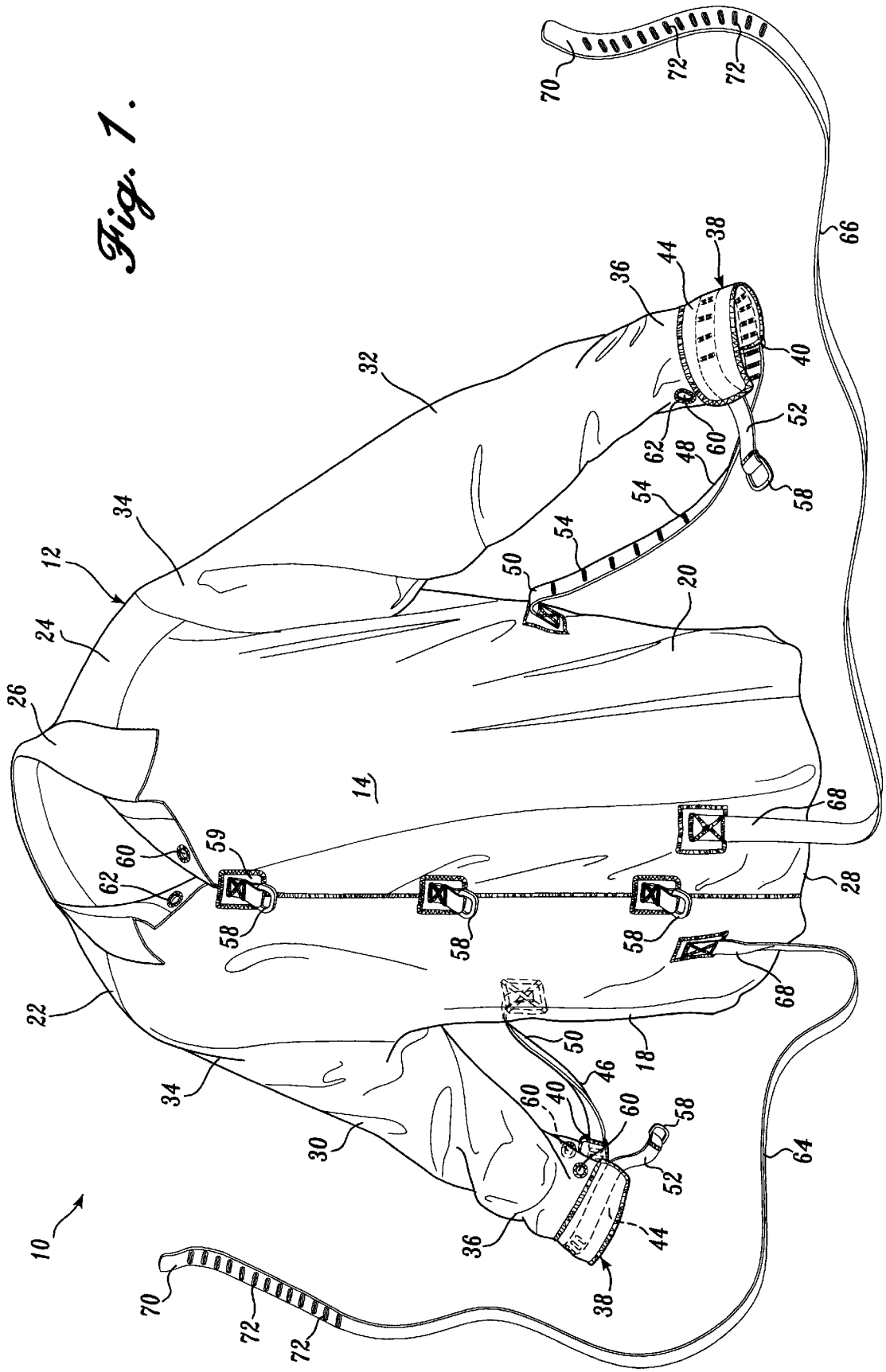
FIG. 1 is a front view of the preferred embodiment of the restraining garment of the present invention.
Figure 2:
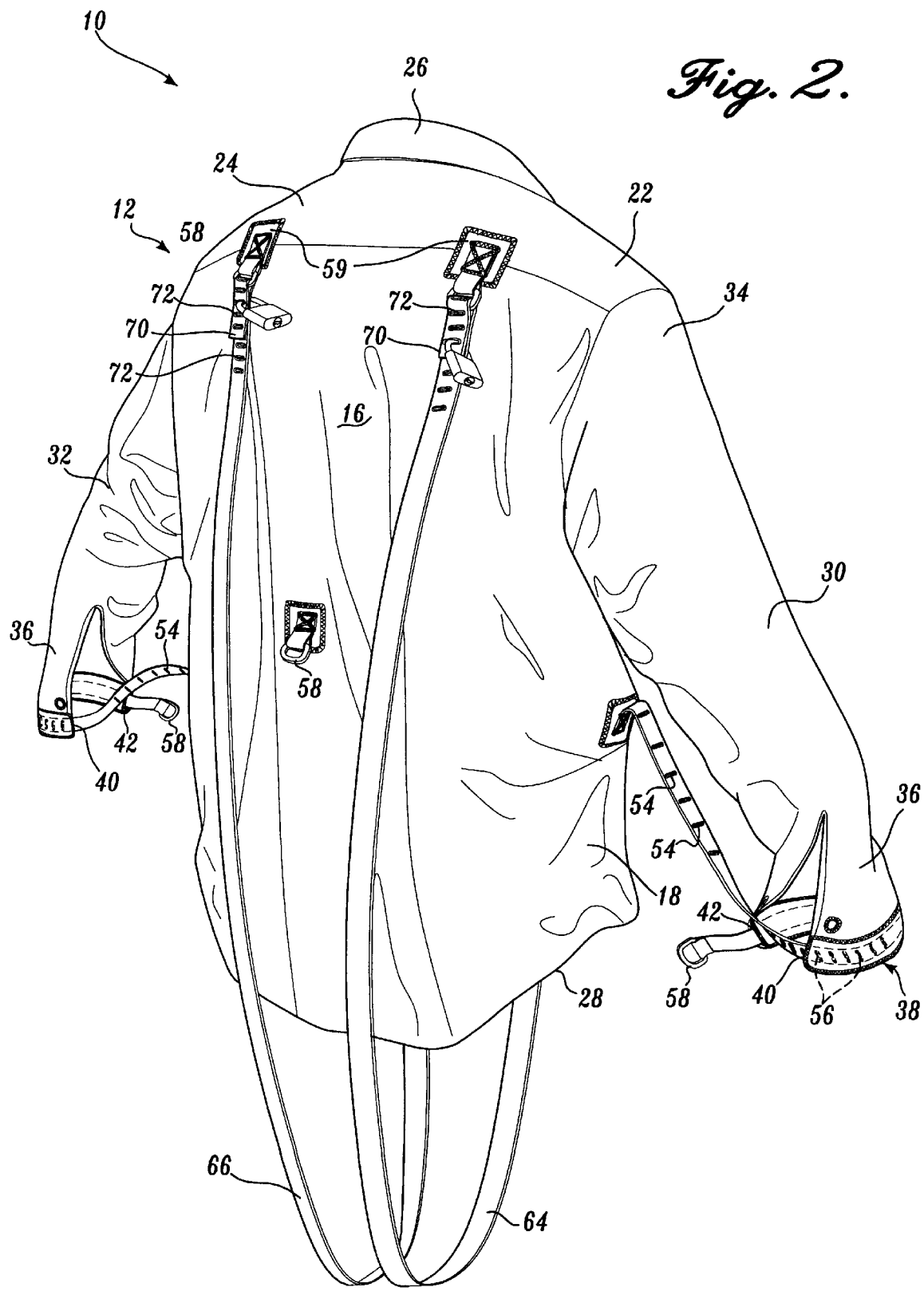
FIG. 2 is a rear view of the preferred embodiment of the restraining garment of the present invention.
Figure 3:
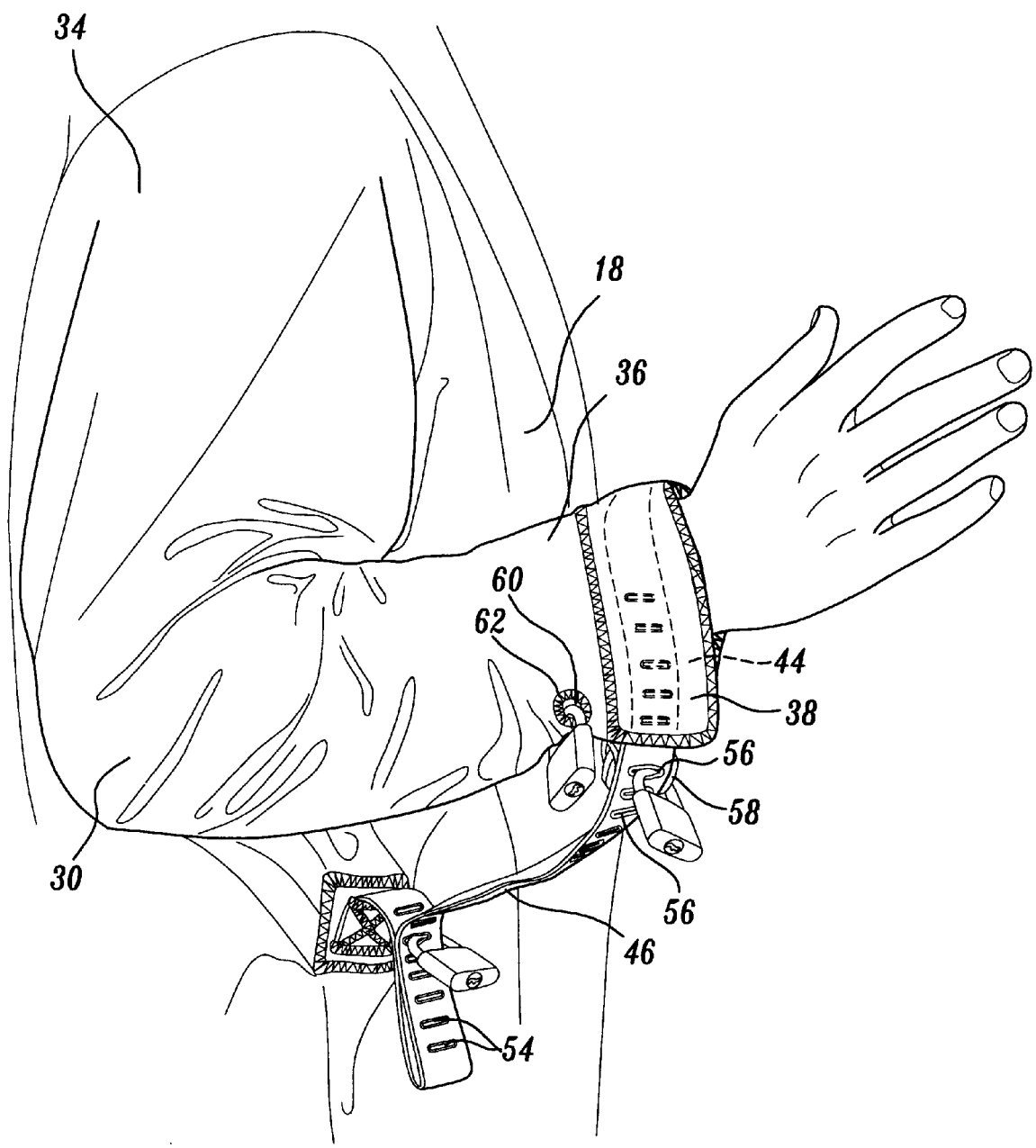
FIG. 3 is a side view of the preferred embodiment of the restraining garment of the present invention showing a wearer's right arm secured within the first sleeve.

With reference to FIGS. 1–3, in particular to FIG. 1, the preferred embodiment of the restraining garment of the present invention is in the form of a restraining shirt 10 which includes a body 12 having a front portion 14, a rear portion 16, a right side 18 and a left side 20. Body 12 further includes right shoulder 22, left shoulder 24, collar 26 and lower margin 28. Restraining shirt 10 also includes a right sleeve 30 and a left sleeve 32. Each of right sleeve 30 and left sleeve 32 includes a proximal end 34 and a distal end 36. Proximal end 34 of right sleeve 30 is fixedly attached to body 12 in the region of right shoulder 22, while proximal end 34 of left sleeve 32 is fixedly attached to body 12 in the region of left shoulder 24. Distal end 36 of each of right sleeve 30 and left sleeve 32 includes a reinforced cuff 38. The circumference of reinforced cuff 38 is discontinuous, being open at the portion closest to body 12. Reinforced cuff 38 is penetrated by a first opening 40 and a second opening 42 and defines a passage 44 therebetween that extends within and around reinforced cuff 38.

Additionally, restraining shirt 10 further includes a right arm strap 46 and a left arm strap 48. Right arm strap 46 and left arm strap 48 are identical, each having a proximal end 50 and a distal end 52. Proximal end 50 of right arm strap 46 is fixedly attached, for example by stitching, to right side 18 of body 12, and proximal end 50 of left arm strap 48 is fixedly attached, for example by stitching, to left side 20 of body 12. Further, right arm strap 46 and left arm strap 48 each define a first plurality of slots 54, located close to arm strap proximal end 50, and a second plurality of slots 56 located close to arm strap distal end 52. A rigid loop 58 is attached to distal end 52 of each of right arm strap 46 and left arm strap 48.

Body 12 also bears a plurality of rigid loops 58 attached to both front portion 14 and rear portion 16. As shown in FIG. 1, preferably three rigid loops 58 are securely attached along the vertical midline of front portion 14 of body 12. As shown in FIG. 2, preferably a rigid loop 58 is securely attached to body rear portion 16 close to each of right shoulder 22 and left shoulder 24 and, additionally, a rigid loop 58 is preferably securely attached to body rear portion 16 at a point along the vertical midline of rear portion 16 located close to the vertical midpoint of the wearer's back. Rigid loops 58 are preferably attached to reinforced patches 59 on body 12. It will be appreciated that while loops 58 are preferably made from a rigid material, loops 58 can also be made from a flexible, or pliable, material, such as denim, provided that the material is sufficiently strong to resist any attempt by the restrainee to tear loops 58.

The preferred embodiment of restraining shirt 10 also includes a plurality of holes 60 each having a reinforced circumference 62. Holes 60 are arranged as three pairs with one pair defined by the portion of collar 26 closest to body front portion 14; another pair of holes 60 is defined by distal end 36 of right sleeve 30, and another pair of holes 60 is defined by distal end 36 of left sleeve 32. In the preferred embodiment shown in FIGS. 1–3, holes 60 defined by distal end 36 of right sleeve 30, and by distal end 36 of left sleeve 32, penetrate sleeve distal end 36 close to reinforced cuff 38. It is within the scope of the invention, however, to have holes 60 that penetrate reinforced cuffs 38, of right sleeve 30 and left sleeve 32, adjacent to, but not penetrating, reinforced cuff passage 44. While reinforced cuffs 38 are shown in FIGS. 1–3 as having the side closest to body 12 being open, reinforced cuffs 38 need not have an open configuration but can, for example, have a continuous, unbroken circumference. In this configuration, reinforced cuffs 38 would preferably define two openings through which arm strap distal end 52 enters and exits reinforced cuff passage 44. Reinforced cuff 38 can optionally be elasticated.

Additionally, restraining garment 10 further includes a right crotch strap 64 and a left crotch strap 66, each having a first end 68 and a second end 70. First end 68 of each of right crotch strap 64 and left crotch strap 66 are fixedly attached to body front portion 14, close to lower margin 28, for example by stitching. The portion of each of right crotch strap 64 and left crotch strap 66 close to crotch strap second end 70 defines a plurality of slots 72.

The operation of restraining shirt 10 will now be considered in detail. Distal end 52 of right arm strap 46 is inserted into first opening 40 of reinforced cuff 38 of right sleeve 30 and threaded through reinforced cuff passage 44 until distal end 52 exits reinforced cuff passage 44. A securing device, preferably a padlock, is inserted through rigid loop 58, located on the terminus of distal end 52 of right arm strap 46, and also through an adjacent slot of second plurality of slots 56 defined by distal end 52 of right arm strap 46. The slot through which the securing device is inserted is selected so that when the securing device is fixed in place, reinforced cuff 38 is drawn sufficiently tightly around the wrist of the wearer that the wearer's right arm is secured within right sleeve 30, but not so tightly that flow of blood through the wearer's right wrist and hand is impeded. A similar procedure is completed with respect to left sleeve 32 thereby securing the wearer's left arm within left sleeve 32. It is understood that the temporal sequence of securing the wearer's right and left arms within restraining shirt 10 is not crucial. The wearer's right arm may be first secured within right sleeve 30, or the wearer's left arm may be first secured within left sleeve 32, or the wearer's right and left arms may simultaneously be secured within right sleeve 30 and left sleeve 32, respectively.

The wearer is prevented from pulling restraining shirt 10 over his or her head by passing right crotch strap 64 and left crotch strap 66 between the wearer's legs and securely attaching, preferably by means of a padlock, second end 70 of right crotch strap 64 and second end 70 of left crotch strap 66 to rigid loops 58 attached to body rear portion 16 close to right shoulder 22 and left shoulder 24, respectively. FIG. 2 shows right crotch strap 64 and left crotch strap 66 secured to rigid loops 58 located close to right shoulder 22 and left shoulder 24, respectively. Preferably, restraining shirt 10 will be tucked into a pair of trousers worn by the restrained person. Consequently, the trousers will preferably be lowered while right crotch strap 64 and left crotch strap 66 are secured in the aforementioned manner, and the trousers will then be raised and secured over and around lower margin 28 of restraining shirt 10.

An advantage to having the restrained person wearing restraining shirt 10 tucked into a pair of trousers is that it is more difficult for the restrained person to extricate his or her legs from right crotch strap 64 and left crotch strap 66 when right crotch strap 64 and left crotch strap 66 are disposed beneath trousers. Further, when right crotch strap 64 and left crotch strap 66 are secured to the wearer inside a pair of trousers, the wearer can drop his or her trousers in order to urinate and/or defecate. Consequently, when restraining shirt 10 is tucked into a pair of trousers, it is preferable that right crotch strap 64 and left crotch strap 66 should not be so tightly drawn against the crotch of the wearer that the wearer is prevented from pushing them aside when defecating or urinating. Although restraining shirt 10 is preferably tucked into a pair of trousers worn by the restrained person, it is understood that restraining shirt 10 need not be tucked into a pair of trousers worn by the restrained person, and that restraining shirt 10 can be worn with articles of clothing other than trousers.

The wearer of restraining shirt 10 may be further restrained in several ways, or by any combination thereof By way of non-limiting example, and as shown in FIG. 3, the degree of arm movement of the wearer's right arm can be further limited by inserting and securing a securing device, such as a padlock, through any two slots of first plurality of slots 54 defined by right arm strap 46. In this way, the length of right arm strap 46 is shortened by the distance between the two slots into which the securing device is inserted. Thus, for example, by inserting a padlock through the first and last of the slots comprising first plurality of slots 54 of right arm strap 46, the wearer's right arm is restrained close to the wearer's body and the amount of arm movement is minimized. Conversely, by inserting a padlock through two adjacent slots within first plurality of slots 54 of right arm strap 46, right arm strap 46 is shortened only slightly and the wearer's right arm movement is minimally restricted. This method can be used to selectively shorten the length of either or both of right arm strap 46 and/or left arm strap 48.

Additionally, the wearer's arm movements can be further restricted by attaching either or both of right sleeve 30 and/or left sleeve 32 to one or more rigid loop 58 located on body 12. Thus, for example, to secure the wearer's right arm to a rigid loop 58 located on the vertical midline of body front portion 14, a securing device, such as a padlock, can be inserted through rigid loop 58 located at the terminus of distal end 52 of right arm strap 46, and through one of the slots comprising second plurality of slots 56, located close to distal end 52 of right arm strap 46, and through a rigid loop 58 located on the vertical midline of body front portion 14. The securing device, such as a padlock, is then secured in place, for example by locking the padlock, thereby restraining the wearer's right hand and wrist against the front of his or her torso. The foregoing procedure can be used to restrain either or both of the wearer's arms to a rigid loop 58 located on body front portion 14 or body rear portion 16.

Alternatively, for example, when it is desired to extensively restrain the wearer, the wearer's arms can be secured within right sleeve 30 and left sleeve 32, as previously described, and handcuffs, flex-cuffs or a similar securing device, can be threaded through a rigid loop 58 located on front portion 14 or rear portion 16 of body 12. The handcuffs, flex-cuffs or similar securing device can be secured around the wearer's wrists thereby restraining the wearer's arms and hands close to the front or back of his or her torso.

There are several advantages associated with having a plurality of rigid loops 58 located along the vertical midline of body front portion 14. For example, a restrainee having a distended abdomen would likely experience considerable discomfort if his or her wrists were attached to a rigid loop 58 located close to lower margin 28 of body front portion 14. In this position, the wearer's arms and wrists would be drawn tightly around and under the extended abdominal region causing pain and discomfort. It would be more humane to attach the wearer's wrists to a rigid loop 58 located above the abdominal region. Additionally, when the wearer's wrists are attached to a rigid loop 58 located above the abdominal region of body front portion 14, it is easier for the person in charge of the restrainee to see what the restrainee is doing with his or her hands.

Restraining shirt 10 is constructed from a rip-resistant material in order to resist any attempt by the wearer to rip the material and so escape from restraining shirt 10. Rip-resistant materials useful in the construction of restraining shirt 10 include, but are not limited to, denim, a Rip-Stop nylon material or a taffeta material. Additionally, it is important that all the seams in restraining shirt 10 be sufficiently strong to resist any attempt by the wearer to tear them and so escape from restraining shirt 10. Seams may be strengthened by any art-recognized means such as, for example, by multiple layers of stitching.

It will be appreciated that, while the preferred embodiment of the restraining garment of the present invention is in the form of restraining shirt 10, the restraining garment of the present invention can be in the form of numerous different types and styles of clothing. For example, minor changes in the design of restraining shirt 10 shown in FIGS. 1–3 would result in a short jacket that could be made, for example, from denim. Additionally, the scope of the present invention includes a garment having legs, such as a boilersuit, ski-suit or jump suit. Further, the restraining garment of the present invention can be made in a range of sizes to accommodate wearers who differ in size, shape and gender.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

What is claimed is:

1. A garment for restraining a person comprising:
   a body;
   a first sleeve having a proximal end and a distal end, said first sleeve proximal end being attached to the body;
   a second sleeve having a proximal end and a distal end, said second sleeve proximal end being attached to the body;
   a first arm strap comprising a proximal end attached to the body and a distal end connectable to a portion of the first sleeve that is closer to the first sleeve distal end than to the first sleeve proximal end, said first arm strap having a length that is insufficient to permit a garment wearer to fully extend said first sleeve to form a right angle with respect to said body when said first arm strap is connected to said first sleeve; and
   a second arm strap comprising a proximal end attached to the body and a distal end connectable to a portion of the second sleeve that is closer to the second sleeve distal end than to the second sleeve proximal end, said second arm strap having a length that is insufficient to permit a garment wearer to fully extend said second sleeve to form a right angle with respect to said body when said second arm strap is connected to said second sleeve.

2. The garment of claim 1 wherein the body further comprises at least one attachment site for a securing device.

3. The garment of claim 1 wherein the first and second arm straps each further comprise at least one attachment site for a securing device.

4. The garment of claim 1 wherein the first and second arm straps each further comprise at least two slots, the length of either of said first and second arm straps being reducible by a desired amount by inserting a securing device through at least two of said slots.

5. The garment of claim 1 further comprising at least one crotch strap.

6. The garment of claim 5 wherein the crotch strap includes a first end and a second end, said first end being attached to the body, said second end including at least one attachment site for a securing device.

7. The garment of claim 1 wherein the distal end of each of the first and second sleeves each includes a cuff defining a passage.

8. The garment of claim 7 wherein each of the cuff passages includes a first opening and a second opening, and the first and second arm straps each include a proximal end, attached to the body, and a distal end received within either of said cuff passage first and second openings.

9. The garment of claim 1 wherein the garment is made from a rip-resistant material.

10. A garment for restraining a person comprising:
   a body, said body having at least one attachment site for a securing device;
   a first sleeve having a proximal end and a distal end, said first sleeve proximal end being attached to the body;
   a second sleeve having a proximal end and a distal end, said second sleeve proximal end being attached to the body;
   a first arm strap comprising a proximal end attached to the body and a distal end connectable to a portion of the first sleeve that is closer to the first sleeve distal end than to the first sleeve proximal end, said first arm strap having a length that is insufficient to permit a garment wearer to fully extend said first sleeve to form a right angle with respect to said body when said first arm strap is connected to said first sleeve; and a second arm strap comprising a proximal end attached to the body and a distal end connectable to a portion of the second sleeve that is closer to the second sleeve distal end than to the second sleeve proximal end, said second arm strap having a length that is insufficient to permit a garment wearer to fully extend said second sleeve to form a right angle with respect to said body when said second arm strap is connected to said second sleeve.

11. A garment for restraining a person comprising:

a body, said body having at least one attachment site for a securing device;

a first sleeve having a proximal end and a distal end, said first sleeve proximal end being attached to the body;

a second sleeve having a proximal end and a distal end, said second sleeve proximal end being attached to the body;

a first arm strap comprising a proximal end attached to the body and a distal end connectable to a portion of the first sleeve that is closer to the first sleeve distal end than to the first sleeve proximal end, said first arm strap having a length that is insufficient to permit a garment wearer to fully extend said first sleeve to form a right angle with respect to said body when said first arm strap is connected to said first sleeve;

a second arm strap comprising a proximal end attached to the body and a distal end connectable to a portion of the second sleeve that is closer to the second sleeve distal end than to the second sleeve proximal end, said second arm strap having a length that is insufficient to permit a garment wearer to fully extend said second sleeve to form a right angle with respect to said body when said second arm strap is connected to said second sleeve; and the first and second arm straps each including at least one attachment site for a securing device.

12. A garment for restraining a person comprising:

a body, said body having at least one attachment site for a securing device;

a first sleeve having a proximal end and a distal end, said first sleeve proximal end being attached to the body;

a second sleeve having a proximal end and a distal end, said second sleeve proximal end being attached to the body;

a first arm strap comprising a proximal end attached to the body and a distal end connectable to a portion of the first sleeve that is closer to the first sleeve distal end than to the first sleeve proximal end, and further comprising at least one attachment site for a securing device, said first arm strap having a length that is insufficient to permit a garment wearer to fully extend said first sleeve to form a right angle with respect to said body when said first arm strap is connected to said first sleeve;

a second arm strap comprising a proximal end attached to the body and a distal end connectable to a portion of the second sleeve that is closer to the second sleeve distal end than to the second sleeve proximal end, and further comprising at least one attachment site for a securing device, said second arm strap having a length that is insufficient to permit a garment wearer to fully extend said second sleeve to form a right angle with respect to said body when said second arm strap is connected to said second sleeve; and at least one crotch strap, said crotch strap having a first end and a second end, said first end being attached to the body, said second end including at least one attachment site for a securing device.

* * * * *